United States Patent
Nakama

(10) Patent No.: US 10,274,447 B2
(45) Date of Patent: Apr. 30, 2019

(54) THERMAL CONDUCTIVITY DETECTOR AND GAS CHROMATOGRAPH

(71) Applicant: SHIMADZU CORPORATION, Kyoto-shi, Kyoto (JP)

(72) Inventor: Yuji Nakama, Kyoto (JP)

(73) Assignee: SHIMADZU CORPORATION, Kyoto-shi (JP)

(*) Notice: Subject to any disclaimer, the term of this patent is extended or adjusted under 35 U.S.C. 154(b) by 156 days.

(21) Appl. No.: 15/665,712

(22) Filed: Aug. 1, 2017

(65) Prior Publication Data

US 2018/0067068 A1   Mar. 8, 2018

(30) Foreign Application Priority Data

Sep. 8, 2016 (JP) .................................. 2016-175106

(51) Int. Cl.
*G01N 27/18* (2006.01)
*G01N 25/18* (2006.01)
*G01N 30/66* (2006.01)
*G01N 30/02* (2006.01)
*G01N 30/12* (2006.01)

(52) U.S. Cl.
CPC ............. *G01N 27/18* (2013.01); *G01N 25/18* (2013.01); *G01N 30/66* (2013.01); *G01N 2030/025* (2013.01); *G01N 2030/126* (2013.01)

(58) Field of Classification Search
None
See application file for complete search history.

(56) References Cited

U.S. PATENT DOCUMENTS

| | | | | |
|---|---|---|---|---|
| 4,316,382 A * | 2/1982 | Woodruff | .............. | G01N 27/18 73/23.2 |
| 4,670,220 A * | 6/1987 | Wells | ................... | G01N 30/20 422/543 |
| 6,928,858 B2 * | 8/2005 | Lin | ........................ | G01N 27/18 422/83 |
| 7,185,527 B2 | 3/2007 | Lin | | |
| 8,549,894 B2 * | 10/2013 | Hoogerwerf | ........... | G01N 30/32 73/23.42 |
| 9,128,028 B2 * | 9/2015 | McBrady | ................ | G01N 30/66 |
| 9,835,574 B2 * | 12/2017 | Biancolillo | ............ | G01N 27/18 |
| 10,031,095 B2 * | 7/2018 | Hill | ........................ | G01N 25/18 |
| 10,060,866 B2 * | 8/2018 | Gellert | ................... | G01N 25/18 |

(Continued)

*Primary Examiner* — Peter J Macchiarolo
*Assistant Examiner* — Jermaine L Jenkins
(74) *Attorney, Agent, or Firm* — Westerman, Hattori, Daniels & Adrian, LLP

(57) ABSTRACT

Detection sensitivity of a single-filament thermal conductivity detector is to be increased. A thermal conductivity detector is a single-filament thermal conductivity detector, and includes a measurement cell, a phase switching mechanism, and a measurement section. The measurement section starts measurement of thermal conductivity of a sample gas after a lapse of a sample gas measurement start time that is set in advance, after a reference phase is switched to a sample phase by the phase switching mechanism, and starts measurement of thermal conductivity of a reference gas after a lapse of a reference gas measurement start time that is set in advance as a length of time different from the sample gas measurement start time, after the sample phase is switched to the reference phase by the phase switching mechanism.

10 Claims, 3 Drawing Sheets

(56) References Cited

U.S. PATENT DOCUMENTS

| | | | |
|---|---|---|---|
| 10,126,277 B2* | 11/2018 | Gellert | G01N 30/62 |
| 2016/0103105 A1* | 4/2016 | Nakama | G01N 30/62 |
| | | | 73/23.4 |
| 2017/0016840 A1* | 1/2017 | Bourlon | G01N 33/0004 |
| 2017/0030873 A1* | 2/2017 | Gellert | B01L 3/5027 |

* cited by examiner

THERMAL CONDUCTIVITY DETECTOR AND GAS CHROMATOGRAPH

BACKGROUND OF THE INVENTION

1. Field of the Invention

The present invention relates to a thermal conductivity detector, and a gas chromatograph provided with the thermal conductivity detector.

2. Description of the Related Art

A thermal conductivity detector determines thermal conductivity of a gas flowing through a measurement channel where a filament is arranged, by causing the gas to flow through the measurement channel and detecting the amount of change in the resistance value of the filament at the time, and thereby obtains a chromatogram. When a gas is caused to flow through the measurement channel where a heated filament is arranged, the heat of the filament is removed due to the thermal conductivity of the gas, and the resistance value of the filament is changed. A chromatogram may be obtained by measuring how much a filament resistance value at the time of flow of a gas containing a sample (sample gas) has changed from a resistance value at the time of flow of a carrier gas not containing the sample (reference gas).

To perform measurement of a sample gas and a reference gas in parallel, there are single-filament thermal conductivity detector and a multi-filament thermal conductivity detector. A multi-filament thermal conductivity detector includes a channel through which a sample gas is to flow and a channel through which a reference gas is to flow, and a filament is arranged in each channel. This type of thermal conductivity detector has an advantage that a sample gas and a reference gas can be simultaneously measured, but because it is not possible to fabricate two filaments with perfectly matching properties regarding temperature characteristics and the like, there is a problem that a slight difference is present between the filament for sample gas measurement and the filament for reference gas measurement, and the difference may result in variance in measurement sensitivity or a drift over time in the chromatogram.

A single-filament thermal conductivity detector includes only one measurement channel where a filament is arranged, and a sample gas and a reference gas are introduced into the measurement channel in a periodically alternating manner (see U.S. Pat. No. 7,185,527). Because measurement of a sample gas and a reference gas is performed using the same filament, variance in the measurement sensitivity between sample gas measurement and reference gas measurement is suppressed, and further, drift over time in the chromatogram may be removed by determining a difference between data at the time of sample gas measurement and data at the time of reference gas measurement.

To alternately introduce a sample gas and a reference gas into the measurement channel, the single-filament thermal conductivity detector includes a reference gas introduction section at each of a position which is closer to the measurement channel than a sample gas introduction section is and a position which is farther away from the measurement channel than the sample gas introduction section is. When a reference gas is introduced from the position which is closer to the measurement channel than the sample gas introduction section is, the reference gas flows through the measurement channel, and a sample gas is caused, by the pressure of the reference gas, to flow through a bypass channel, which is provided opposite the measurement channel across the sample gas introduction section. On the other hand, if a reference gas is introduced from the position which is farther away from the measurement channel than the sample gas introduction section is, a sample gas flows through the measurement channel, and the reference gas flows through the bypass channel.

In this manner, a state where a sample gas flows through the measurement channel (sample phase) and a state where a reference gas flows through the measurement channel (reference phase) are periodically switched between each other, and signals obtained in the respective phases are alternately acquired. A drift over time can be removed by determining a difference between the signals acquired in the sample phase and the reference phase, and thus, stability is extremely high.

According to U.S. Pat. No. 7,185,527, switching of a solenoid valve for switching the introduction position of a reference gas is periodically performed at the time of normal analysis, but when a sample gas (with saturated signal) that damages the filament flows through, the state where a reference gas flows through the measurement channel (reference phase) is established to prevent the sample gas that damages the filament from flowing through the measurement channel so that the damage on the filament is reduced.

SUMMARY OF THE INVENTION

The present invention has its object to enable an increase in the detection sensitivity of a single-filament thermal conductivity detector as described above.

A thermal conductivity detector according to the present invention is a single-filament thermal conductivity detector, and includes a measurement cell, a phase switching mechanism, and a measurement section. The measurement cell includes a measurement channel where a filament is arranged, a gas introduction channel, having one end connected to the measurement channel, for supplying a gas to the measurement channel, a bypass channel, connected to another end of the gas introduction channel, where a filament is not arranged, a sample gas introduction section for introducing a sample gas into the gas introduction channel, a first reference gas introduction section for introducing a reference gas into the gas introduction channel from a position, of the gas introduction channel, that is closer to the measurement channel than the sample gas introduction section is, and a second reference gas introduction section for introducing a reference gas into the gas introduction channel from a position, of the gas introduction channel, that is closer to the bypass channel than the sample gas introduction section is. The measurement cell is configured such that a sample gas flows through the bypass channel when a reference gas is introduced into the gas introduction channel from the first reference gas introduction section, and a sample gas flows through the measurement channel when a reference gas is introduced into the gas introduction channel from the second reference gas introduction section.

The phase switching mechanism switches an introduction position of a reference gas between the first reference gas introduction section and the second reference gas introduction section so as to selectively switch to either a reference phase in which a reference gas is introduced into the gas introduction channel from the first reference gas introduction section or a sample phase in which a reference gas is introduced into the gas introduction channel from the second reference gas introduction section.

The measurement section captures a signal that is based on a resistance value of the filament, and measures thermal conductivity of a fluid flowing through the measurement channel, based on an amount of change in the resistance value of the filament.

As described above, the measurement cell of a single-filament type includes a reference gas introduction section at each of a position that is closer to the measurement channel than the sample gas introduction section is and a position that is farther away from the measurement channel than the sample gas introduction section is, and in the reference phase, a reference gas is introduced from the first reference gas introduction section, which is closer to the measurement channel than the sample gas introduction section is. Accordingly, the time required to replace all the gas in the measurement channel by a sample gas after switching to the sample phase and the time required to replace all the gas in the measurement channel by a reference gas after switching to the reference phase are different from each other.

Conventionally, a sufficient time for replacing all the gas in a measurement channel by a sample gas or a reference gas is estimated, and a signal from a filament is captured and measurement of thermal conductivity of a gas is started, in either phase, after waiting for a lapse of a specific period of time after switching of the phases. However, as described above, the time required for all the gas in the measurement channel to be replaced is different between the sample phase and the reference phase, and a wasteful standby time is caused in at least one of the phases. The present inventor(s) has/have found that the detection sensitivity can be increased by reducing the wasteful standby time.

The measurement section of the thermal conductivity detector according to the present invention starts measurement of thermal conductivity of a sample gas after a lapse of a sample gas measurement start time that is set in advance, after the reference phase is switched to the sample phase by the phase switching mechanism, and starts measurement of thermal conductivity of a reference gas after a lapse of a reference gas measurement start time that is set in advance as a length of time different from the sample gas measurement start time, after the sample phase is switched to the reference phase by the phase switching mechanism.

That is, according to the thermal conductivity detector of the present invention, the sample gas measurement start time, which is the standby time from switching from the reference phase to the sample phase until thermal conductivity measurement for a sample gas is started, and the reference gas measurement start time, which is the standby time from switching from the sample phase to the reference phase until thermal conductivity measurement for a reference gas is started, are different from each other.

In the reference phase, a reference gas is introduced into the measurement channel from the reference gas introduction section that is provided at a position closer than the sample gas introduction section, and thus, the time required for all the gas in the measurement channel to be replaced by the reference gas is shorter than the time required to replace all the gas in the measurement channel by a sample gas. Therefore, the reference gas measurement start time is preferably set shorter than the sample gas measurement start time. This allows a wasteful standby time in the reference phase to be reduced.

In a more preferred aspect, the sample gas measurement start time is set taking into account a time required by a reference gas in the measurement channel to be replaced by a sample gas introduced from the sample gas introduction section, and the reference gas measurement start time is set taking into account a time required by a sample gas in the measurement channel to be replaced by a reference gas introduced from the first reference gas introduction section. This allows a wasteful standby time to be reduced in both the sample phase and the reference phase.

As described above, if a wasteful standby time is reduced in each phase, the reference gas measurement start time in the reference phase becomes shorter than the sample gas measurement start time in the sample phase. Accordingly, if the same length of time is secured as the measurement time in each phase, the reference phase becomes shorter than the sample phase. Therefore, according to the thermal conductivity detector of the present invention, the phase switching mechanism may switch the introduction position of a reference gas between the first reference gas introduction section and the second reference gas introduction section in such a way that the sample phase is made longer than the reference phase.

A gas chromatograph according to the present invention includes a sample vaporization section for vaporizing a sample, and for causing the sample after vaporization to be mixed with a carrier gas and to be supplied as a sample gas, and a detector for detecting each sample component separated by an analytical column, where the thermal conductivity detector described above is used as the detector.

According to the thermal conductivity detector of the present invention, the sample gas measurement start time, which is the standby time from switching from the reference phase to the sample phase until thermal conductivity measurement for a sample gas is started, and the reference gas measurement start time, which is the standby time from switching from the sample phase to the reference phase until thermal conductivity measurement for a reference gas is started, are different, and thus, there is a distinction from a case where a uniform standby time is provided in spite of the time required for all the gas in the measurement channel to be replaced being different between the sample phase and the reference phase.

That is, according to the thermal conductivity detector of the present invention, due to the difference in the time required for replacement of gas in the measurement channel, the sample gas measurement start time and the reference gas measurement start time are set to different lengths, and a wasteful standby time may be reduced in at least one of the phases. If a wasteful standby time before start of measurement of thermal conductivity is reduced, the frequency of switching of the phases may be increased to the extent to increase the temporal resolution, or an acquisition time for a signal from the filament may be made longer to increase the S/N. Further, the sensitivity may be increased by optimizing the design by eliminating a wasteful standby time and by increasing the length of the measurement channel so as to arrange a longer filament, for example.

The gas chromatograph according to the present invention includes the thermal conductivity detector described above as the detector, and thus, the detection sensitivity of the detector is increased, and the analysis accuracy is increased.

DETAILED DESCRIPTION OF THE INVENTION

Hereinafter, an embodiment will be described for a thermal conductivity detector and a gas chromatograph provided with the thermal conductivity detector, with reference to the drawings.

Figure 1:
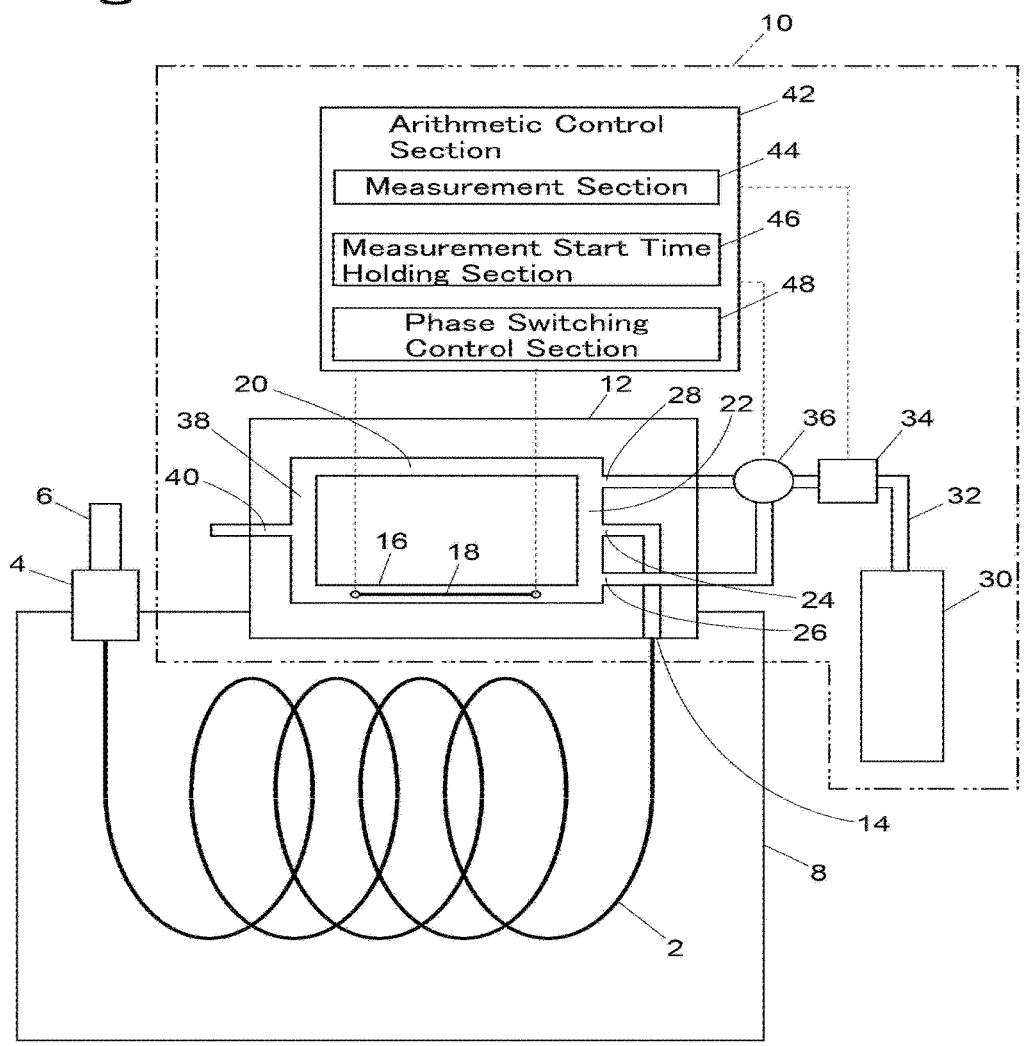
FIG. 1 is a configuration diagram schematically showing an embodiment of a gas chromatograph including a thermal conductivity detector.

First, a gas chromatograph of an embodiment and a thermal conductivity detector used by the gas chromatograph will be described with reference to FIG. 1.

The gas chromatograph has a sample vaporization section 4 connected to one end of an analytical column 2 for separating a sample into components, and a detector 10 connected to the other end of the analytical column 2. The analytical column 2 is housed inside a column oven 8 to have its temperature adjusted. An injector 6 is provided to the sample vaporization section 4, and a sample that is injected from the injector 6 is vaporized inside the sample vaporization section 4, and is guided to the analytical column 2 together with a carrier gas supplied to the sample vaporization section 4. A sample gas introduced into the analytical column 2 is separated into components to be guided and detected by the detector 10.

The detector 10 includes a measurement cell 12 through which the sample gas from the analytical column 2 is to pass. The other end of the analytical column 2 is connected to an inlet port 14 provided to the measurement cell 12. A measurement channel 16 where a filament 18 is arranged and a bypass channel 20 where a filament is not arranged are provided inside the measurement cell 12. One end of the measurement channel 16 and one end of the bypass channel 20 are connected to each other by a gas introduction channel 22, and the other end of the measurement channel 16 and the other end of the bypass channel 20 are connected to each other by a gas discharge channel 38. That is, the measurement channel 16 and the bypass channel 20 are connected to each other in parallel by the gas introduction channel 22 and the gas discharge channel 38.

A sample gas introduction section 24, a first reference gas introduction section 26, and a second reference gas introduction section 28 are provided at mid-portions of gas introduction channel 22. The sample gas introduction section 24 is connected to the inlet port 14 via a channel, and a sample gas from the analytical column 2 is introduced into the gas introduction channel 22 through the sample gas introduction section 24.

The first reference gas introduction section 26 is provided at a position which is closer to the measurement channel 16 than the sample gas introduction section 24 is, and the second reference gas introduction section 28 is provided at a position which is farther away from the measurement channel 16 and closer to the bypass channel 20 than the sample gas introduction section 24 is. The first reference gas introduction section 26 and the second reference gas introduction section 28 are both connected, via a three-way solenoid valve 36, to a reference gas supply channel 32 through which a reference gas from a reference gas cylinder 30 is to flow. A reference gas to be supplied from the reference gas cylinder 30 is the same gas as a carrier gas that is supplied to the sample vaporization section 4. The flow rate of a reference gas flowing through the reference gas supply channel 32 is controlled by a pressure control valve 34.

The three-way solenoid valve 36 connects the reference gas supply channel 32 to either a channel communicating with the first reference gas introduction section 26 or a channel communicating with the second reference gas introduction section 28 by selectively switching between the channels. When a reference gas is introduced from the first reference gas introduction section 28 into the gas introduction channel 22, the pressure on the side of the measurement channel 16 is increased compared with the pressure on the side of the bypass channel 20. Accordingly, a state (reference phase) is achieved where a sample gas introduced from the sample gas introduction section 24 flows through the bypass channel 20 and the reference gas flows through the measurement channel 16. In contrast, when a reference gas is introduced from the second reference gas introduction section 28 into the gas introduction channel 22, the pressure on the side of the bypass channel 20 is increased compared with the pressure on the side of the measurement channel 16. Accordingly, a state (sample phase) is achieved where a sample gas introduced from the sample gas introduction section 24 flows through the measurement channel 16.

That is, the three-way solenoid valve 36 forms a phase switching mechanism for switching to either the sample phase or the reference phase by switching the introduction position of the reference gas to the gas introduction channel 22. Additionally, the phase switching mechanism is not limited to a type that uses a valve, and may adopt any type as long as a gas that flows through the measurement channel 16 can be switched between a sample gas and a reference gas.

A gas which has flowed through the measurement channel 16 and the bypass channel 20 is discharged outside through an outlet section 40 provided to the gas discharge channel 38.

The thermal conductivity detector 10 further includes an arithmetic control section 42. The arithmetic control section 42 is realized by a dedicated computer or a general-purpose personal computer. The arithmetic control section 42 includes, as its functions, a measurement section 44, a measurement start time holding section 46, and a phase switching control section 48.

The measurement section 44 reads, as a signal, the resistance value of the filament 18 at a predetermined timing in the sample phase or the reference phase, and measures the electrical conductivity of a sample gas flowing through the measurement channel 16 based on the signal. The time from switching to each of the sample phase and the reference phase to the start of measurement of thermal conductivity is set in advance, and is held in the measurement start time holding section 46 as a sample gas measurement start time and a reference gas measurement start time.

The phase switching control section 48 controls a switching operation of the three-way solenoid valve 36 so that switching between the sample phase and the reference phase is performed at a predetermined timing. A measurement operation of the measurement section 44 for the thermal conductivity is performed in synchronization with the switching operation of the phase switching control section 48 for the phases.

With the thermal conductivity detector 10 of the embodiment, the length of the sample gas measurement start time from switching to the sample phase until measurement of the thermal conductivity is started, and the length of the reference gas measurement start time from switching to the reference phase until measurement of the thermal conductivity is started, are different from each other, and the reference gas measurement start time is set shorter than the sample gas measurement start time. The reason is described with reference to FIGS. 2A and 2B.

Figure 2A:
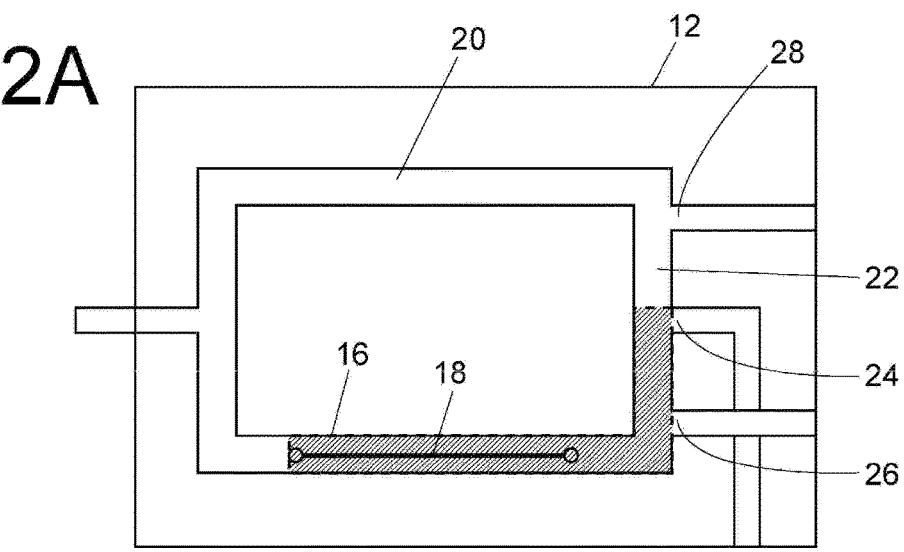
FIGS. 2A and 2B are conceptual diagrams showing (A) a gas replacement volume in a sample phase and (B) a gas replacement volume in a reference phase, respectively, of a measurement cell of the thermal conductivity detector of the present embodiment.
Figure 2B:
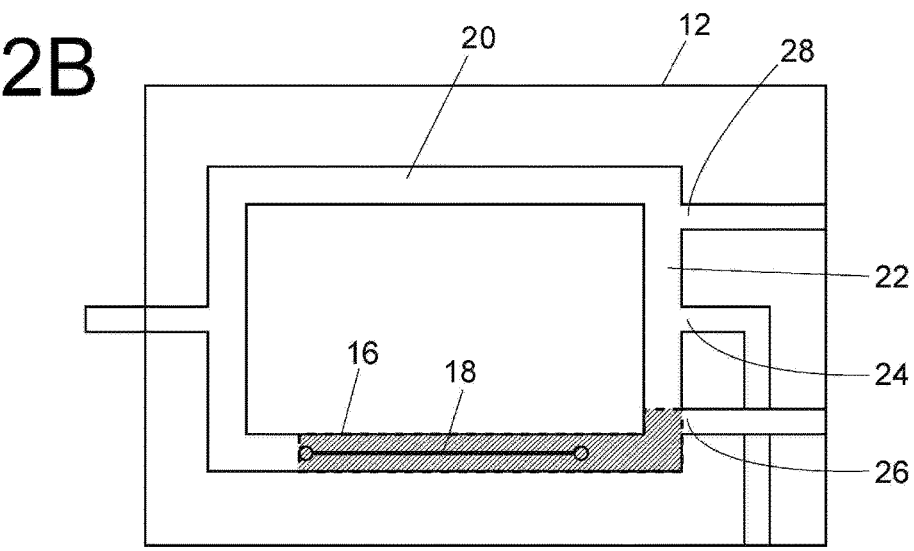

FIGS. 2A and 2B schematically show the volumes inside the channel necessary to replace all the gas in the measurement channel 16 in respective phases, and FIG. 2A shows the sample phase, and FIG. 2B shows the reference phase. In the drawings, hatched regions surrounded by broken lines are regions where the gas has to be replaced at the time of switching to respective phases. As can be seen from the drawings, the amount of sample gas to be introduced, in the sample phase, to replace all the gas in the measurement channel 16 by the sample gas is greater than the amount of reference gas to be introduced, in the reference phase, to replace all the gas in the measurement channel 16 by the reference gas. That is, in the case where the flow rate of the sample gas and the flow rate of the reference gas are the same, the time from switching to the sample phase to when measurement of thermal conductivity is enabled is longer than the time from switching to the reference phase to when measurement of thermal conductivity is enabled.

Figure 3:
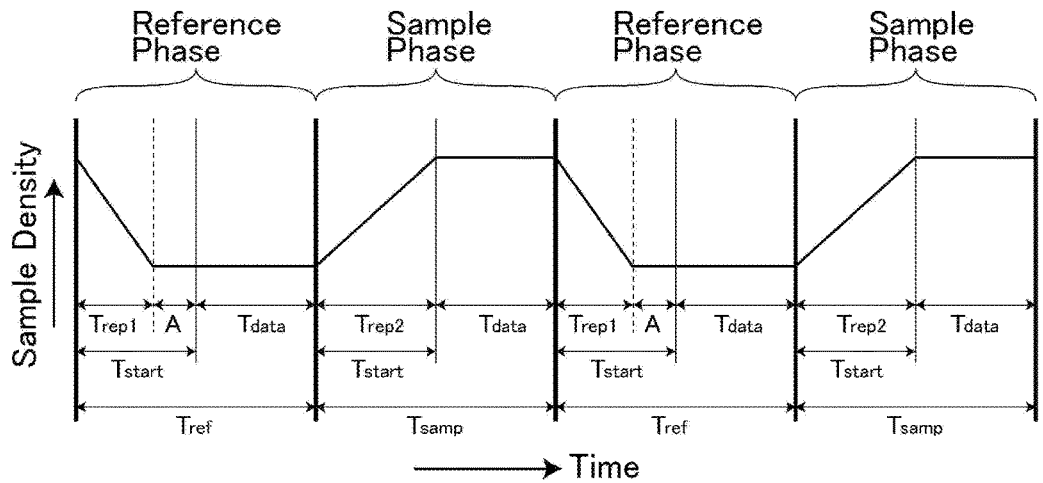
FIG. 3 is a time chart for a case where a measurement start time is uniformly set for phases of the thermal conductivity detector of the present embodiment.

If, in spite of the circumstance described above, a time ($T_{start}$) from switching to a phase to the start of measurement of thermal conductivity is set the same for the sample phase and the reference phase, a wasteful standby time A as shown in the time chart in FIG. 3 is caused. That is, in the reference phase in which a time ($T_{rep1}$) required to replace the gas in the measurement channel 16 is shorter than that ($T_{rep2}$) of the sample phase, because measurement of thermal conductivity is not started even when replacement of gas is completed, standby has to be performed until a lapse of the time A.

Figure 4:
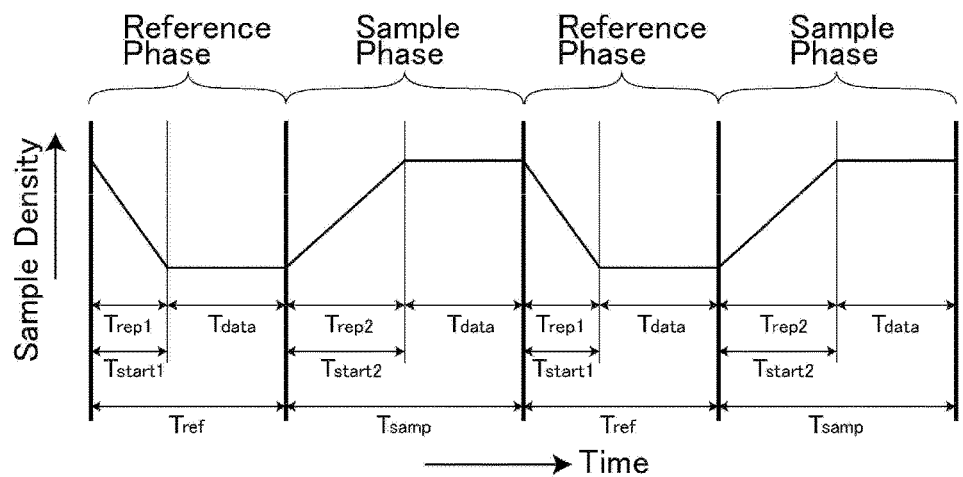
FIG. 4 is a time chart for a case where a measurement start time is non-uniformly set for the phases of the thermal conductivity detector of the present embodiment.

On the other hand, according to the thermal conductivity detector 10 of the embodiment, as shown in the time chart in FIG. 4, a reference gas measurement start time ($T_{start1}$) is set shorter than a sample gas measurement start time ($T_{start2}$) to thereby eliminate the wasteful standby time A. In this embodiment, the reference gas measurement start time ($T_{start1}$) and the sample gas measurement start time ($T_{start2}$) are set taking into account a time ($T_{rep1}$) required to replace the gas in the measurement channel 16 by the reference gas and a time ($T_{rep2}$) required to replace the gas in the measurement channel 16 by the sample gas, respectively. Accordingly, occurrence of a wasteful standby time is prevented in both the reference phase and the sample phase.

In this embodiment, the same length of time is ensured, in the reference phase and the sample phase, as a read time ($T_{data}$) for a signal from the filament 18 by the measurement section 44, and thus, a length ($T_{ref}$) of the reference phase and a length ($T_{samp}$) of the sample phase are different from each other. The phase switching control section 48 of the arithmetic control section 42 controls the timing of switching by the three-way solenoid valve 36 so as to make the lengths of the reference phase and the sample phase different in the above manner.

Eliminating the wasteful standby time A in the reference phase, as described above, enables various modifications for increasing the detection sensitivity of the thermal conductivity detector 10. For example, because the wasteful standby time A is simply eliminated, the phases may be switched at an earlier timing, and the temporal resolution of the detection signal may thereby be increased. Further, if time corresponding to the standby time A is divided and sorted into signal acquisition times ($T_{data}$) of the reference phase and the sample phase, acquisition of signals may be performed over a longer period of time, compared with in the past, without increasing the time of one measurement cycle combining the reference phase and the sample phase, and the S/N may be increased.

Furthermore, because the standby time A is eliminated, the time ($T_{rep1}$) required to replace the gas in the measurement channel 16 by the reference gas and the time ($T_{rep2}$) required to replace the gas in the measurement channel 16 by the sample gas may be made longer without increasing the time of one measurement cycle. That is, the measurement channel 16 may be designed to be longer. If the measurement channel 16 is made longer, a filament 18 that is longer to the extent may be arranged, and the detection sensitivity may be increased, making an improvement regarding the minimum amount of detection.

Additionally, in the embodiment described above, the measurement section 44, the measurement start time 46, and the phase switching control section 48 are provided to the same arithmetic control section 42, but one or some of these sections may be provided as the function of another device.

What is claimed is:

1. A thermal conductivity detector comprising:
a measurement cell including a measurement channel where a filament is arranged, a gas introduction channel, having one end connected to the measurement channel, for supplying a gas to the measurement channel, a bypass channel, connected to another end of the gas introduction channel, where a filament is not arranged, a sample gas introduction section for introducing a sample gas into the gas introduction channel, a first reference gas introduction section for introducing a reference gas into the gas introduction channel from a position, of the gas introduction channel, that is closer to the measurement channel than the sample gas introduction section is, and a second reference gas introduction section for introducing a reference gas into the gas introduction channel from a position, of the gas introduction channel, that is closer to the bypass channel than the sample gas introduction section is, the measurement cell being configured in such a way that a sample gas flows through the bypass channel when a reference gas is introduced into the gas introduction channel from the first reference gas introduction section, and a sample gas flows through the measurement channel when a reference gas is introduced into the gas introduction channel from the second reference gas introduction section;
a phase switching mechanism for switching an introduction position of a reference gas between the first reference gas introduction section and the second reference gas introduction section so as to selectively switch to either a reference phase in which a reference gas is introduced into the gas introduction channel from the first reference gas introduction section or a sample phase in which a reference gas is introduced into the gas introduction channel from the second reference gas introduction section; and
a measurement section for capturing a signal that is based on a resistance value of the filament, and for measuring thermal conductivity of a fluid flowing through the measurement channel, based on an amount of change in the resistance value of the filament,
wherein the measurement section starts measurement of thermal conductivity of a sample gas after a lapse of a sample gas measurement start time that is set in advance, after the reference phase is switched to the sample phase by the phase switching mechanism, and starts measurement of thermal conductivity of a reference gas after a lapse of a reference gas measurement start time that is set in advance as a length of time different from the sample gas measurement start time, after the sample phase is switched to the reference phase by the phase switching mechanism.

2. The thermal conductivity detector according to claim 1, wherein the reference gas measurement start time is set shorter than the sample gas measurement start time.

3. The thermal conductivity detector according to claim 2, wherein the sample gas measurement start time is set taking into account a time required by a reference gas in the measurement channel to be replaced by a sample gas introduced from the sample gas introduction section, and
wherein the reference gas measurement start time is set taking into account a time required by a sample gas in the measurement channel to be replaced by a reference gas introduced from the first reference gas introduction section.

4. The thermal conductivity detector according to claim 3, wherein the phase switching mechanism switches the introduction position of a reference gas between the first reference gas introduction section and the second reference gas introduction section in such a way that the sample phase is made longer than the reference phase.

5. A gas chromatograph comprising:
a sample vaporization section for vaporizing a sample, and for causing the sample after vaporization to be mixed with a carrier gas and to be supplied as a sample gas;
an analytical column for separating the sample in the sample gas from the sample vaporization section into components; and
the thermal conductivity detector, according to claim 3, for detecting each sample component separated by the analytical column.

6. The thermal conductivity detector according to claim 2, wherein the phase switching mechanism switches the introduction position of a reference gas between the first reference gas introduction section and the second reference gas introduction section in such a way that the sample phase is made longer than the reference phase.

7. A gas chromatograph comprising:
a sample vaporization section for vaporizing a sample, and for causing the sample after vaporization to be mixed with a carrier gas and to be supplied as a sample gas;
an analytical column for separating the sample in the sample gas from the sample vaporization section into components; and
the thermal conductivity detector, according to claim 2, for detecting each sample component separated by the analytical column.

8. The thermal conductivity detector according to claim 1, wherein the phase switching mechanism switches the introduction position of a reference gas between the first reference gas introduction section and the second reference gas introduction section in such a way that the sample phase is made longer than the reference phase.

9. A gas chromatograph comprising:
a sample vaporization section for vaporizing a sample, and for causing the sample after vaporization to be mixed with a carrier gas and to be supplied as a sample gas;
an analytical column for separating the sample in the sample gas from the sample vaporization section into components; and
the thermal conductivity detector, according to claim 1, for detecting each sample component separated by the analytical column.

10. A gas chromatograph comprising:
a sample vaporization section for vaporizing a sample, and for causing the sample after vaporization to be mixed with a carrier gas and to be supplied as a sample gas;
an analytical column for separating the sample in the sample gas from the sample vaporization section into components; and
the thermal conductivity detector, according to claim 4, for detecting each sample component separated by the analytical column.

* * * * *